United States Patent [19]

DeTournay

[11] 4,175,431
[45] Nov. 27, 1979

[54] HEAVY DUTY SPRING TESTING APPARATUS AND METHOD

[76] Inventor: Henry R. DeTournay, 441 Mark Dr., Warson Woods, Mo. 63122

[21] Appl. No.: 899,411

[22] Filed: Apr. 24, 1978

[51] Int. Cl.² ............................................. G01N 3/10
[52] U.S. Cl. ..................................................... 73/161
[58] Field of Search ................................. 73/161, 97

[56] References Cited

U.S. PATENT DOCUMENTS

| | | | |
|---|---|---|---|
| 1,768,512 | 6/1930 | DeLeeuw | 73/94 X |
| 2,001,711 | 5/1935 | Dinzl | 73/97 |
| 2,088,372 | 7/1937 | Gogan | 73/161 |
| 2,746,288 | 5/1956 | Scott | 73/161 X |
| 3,233,454 | 2/1966 | McCullough | 73/161 |
| 3,308,654 | 3/1967 | Badgley | 73/94 X |
| 3,628,378 | 12/1971 | Regan, Jr. | 73/93 |

*Primary Examiner*—Charles A. Ruehl
*Attorney, Agent, or Firm*—Richard G. Heywood

[57] ABSTRACT

An apparatus for testing compression and tension springs, comprising a base member having an anchor end with fixed means adjacent thereto to orient one end of a spring to be tested and an actuation end with movable means for orienting the other end of the spring, a pressure system including a fluid pressure cylinder connected to the movable means for effecting longitudinal movement thereof away from the anchor end means, valve means for establishing fluid pressure communication between a pressure source and the pressure cylinder and a pressure gauge responsive to such pressure fluid communication, shut-off valve means for limiting movement of the movable means, and other valve means for releasing pressure from the pressure system; and a method for the comparative testing and mating of springs into matched sets.

6 Claims, 7 Drawing Figures

4,175,431

HEAVY DUTY SPRING TESTING APPARATUS AND METHOD

BACKGROUND OF THE INVENTION

The present invention relates generally to spring testing apparatus, and more particularly to apparatus and methods for testing heavy duty compression and tension springs, bellows and like resilient members.

Compression and tension springs of pre-selected size, length and force are essential to the efficient, safe and optimum performance of most machines and equipment, and matched or "mated" springs having substantially equal characteristics are designated in the standards and specifications of equipment manufacturers. In the automotive field, for instance, matched sets of springs are essential to the proper performance of internal combustion engines, brake systems and the like. Spring manufacturers generally are able to achieve a substantial uniformity in matching spring sets having essentially identical characteristics (within close tolerances) through internal quality control of manufacturing and testing procedures, but even new springs are often mismatched and/or fail to meet the prescribed specifications established for the equipment in which these springs are used.

The problems of unequal or mismatched springs become even more acute through actual usage of the equipment, and resultant uneven wear, damage, fatigue or similar problems in the springs or the equipment parts operated thereby. In automotive brake systems, brake shoe return springs (see FIG. 6) and brake chamber retracting springs (see FIG. 7) can become weak and unmatched due to elongation ("spring stretch"), fatigue or the like, and this may cause erratic performance, slow brake release, uneven wear or uneven brake application and excessive heat buildup. Brake lining wear and unmated springs produce pulling or dragging brake problems and infrequent brake adjustments may result in excessive stretching of the return springs and permanent elongation thereof. These springs also function (stretching and contracting) in the confined heat area of the drum and excessive stretch and heat may produce metal fatigue in the springs. Properly functioning, shoe return springs should react quickly and evenly so that both brakes on the same axle will be balanced. Besides being mated for equal tension, the springs should have the tension of new springs conforming to equipment manufacturers specifications. For instance, the largest manufacturers of transit and highway buses, trucks and tractors use heavy duty Rockwell front and rear axles and mechanical brake systems. The GMC brake specifications for Rockwell axles require front brake shoe return springs (see FIG. 5) having a free length of 8 11/16 inches and a stretch or tension length of 9 13/32 inches with a "pounds-pull" tension of 32 to 38 pounds. The GMC brake specifications for rear brake shoe retraction springs (see FIG. 4) call for a free length of 8½ inches and a stretch length of 9 13/32 inches with a 113 to 137 pound tension. It may be noted that the specified stretch length of both front and rear brake springs is identical despite substantial differences in the relative strength and free length of these springs.

In the servicing of such heavy duty truck brakes or the like, the length and tension of all return springs must be checked and matched pairs of correct springs installed on both brakes of the same axle to assure efficient and safe brake operation. Similarly, the compressive force of conventional brake chamber springs is vital to brake balance since even small variations in tension or force are magnified in operation due to the compounding factors of leverage in driving the slack adjusters to rotate the camshaft for applying the brake shoes. Therefore, the brake chamber springs for both actuators must be checked and mated to each other within the length and tension specifications for proper functioning of both brakes on the same axle.

It will be understood that the necessity for mating brake spring sets to meet the requirements just given for heavy duty air brake systems of commercial buses and heavy over-the-road trucks is equally applicable to the vacuum-actuated hydraulic or straight hydraulic brake systems of medium to light trucks, buses, automobiles and other vehicles and implements in general.

In the past, helical-wound tension springs (single and double coil) have traditionally been tested, if at all, by elementary "fish scale" type devices which themselves are spring loaded and subject to spring elongation and fatigue thereby compounding errors and variations in the test results. Over-reaction to such simplistic methods has resulted in complex, delicate instrumentation and complicated procedures for testing tension and/or compression springs. In short, heretofore there has been no simple, positive acting, spring testing apparatus or method for quickly and easily comparing and mating either compression or tension springs into matched sets.

SUMMARY OF THE INVENTION

The invention is embodied in an apparatus for the comparative testing of both compression and tension springs and comprises a horizontal base member having an anchor end with fixed means adjacent thereto to orient one end of a spring to be tested and an actuation end with movable means for orienting the other end of the spring, a fluid pressure system including pressure responsive actuating means connected to the movable means and adapted to effect linear horizontal movement thereof with respect to the anchor end means for tensioning the spring, first valve means for establishing fluid pressure communication between a pressure source and the actuating means, pressure gauge means responsive to the fluid pressure communication, shut-off valve means for limiting movement of the movable means, and other valve means for releasing pressure from the pressure system. The invention is also embodied in a method for effecting the comparative testing and mating of springs into matched sets.

The principal object of the present invention is to provide improvements in spring testing apparatus and methods for the comparative testing of both compression and tension springs.

Another object is to provide a simple, but highly accurate testing apparatus, particularly adapted to the testing of heavy duty brake springs, and methods of quickly measuring the "pounds pull" of retracting type springs principally used in the automotive field.

Another object is to provide a relatively light weight and portable testing apparatus capable of accurately testing heavy duty springs, and a method of converting air pressure readings to reliable "pounds pull" measurements.

Still another object is to provide apparatus and methods for rapidly testing compression and tension springs used in automotive brake systems to facilitate efficient servicing and maintenance thereof.

Yet another object is to provide a simply calibrated, yet accurate testing apparatus that is quickly adaptable to the testing of springs of different lengths.

These and still other objects and advantages will become more apparent from the following description of the invention as taken in conjunction with the accompanying drawings.

BRIEF DESCRIPTION OF THE DRAWINGS

In the accompanying drawings which form a part of this specification and in which like numerals refer to like parts wherever they occur.

DESCRIPTION OF THE PREFERRED EMBODIMENT

For purposes of disclosure, and before describing the spring testing apparatus 10 embodying the present invention, reference is first made to FIGS. 4-7 showing typical brake springs and the functional use thereof for a better environmental understanding of the importance of this invention.

Figure 4:
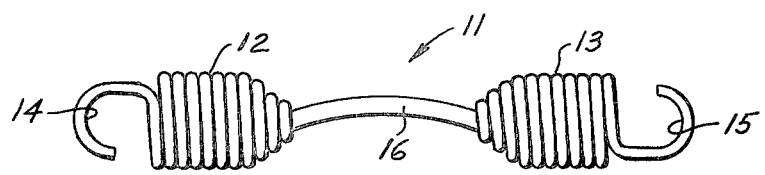
FIG. 4 illustrates one type of typical brake spring to be tested in the present apparatus.

FIG. 4 illustrates a heavy duty, double coil spring 11 having similar left and right-hand coil sections 12,13 with outer attachment hook ends 14,15 and a rigid connecting bar 16 therebetween. This spring 11 is typical of the relatively large, strong brake shoe return springs specified for use in rear brake assemblies 17 (FIG. 6) for Rockwell axles (not shown) of heavy duty trucks and buses. As stated in the "Background of the Invention", the GMC brake specifications for these springs require a free length of 8½ inches and a stretch length of 9 13/32 inches with a tension of 113-137 pounds.

Figure 5:
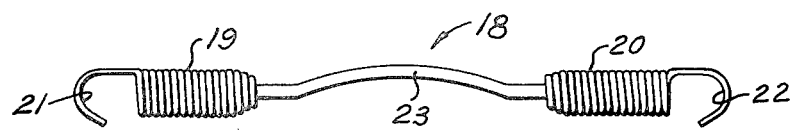
FIG. 5 illustrates another form of typical brake spring to be tested.

FIG. 5 illustrates another form of heavy duty, double coil spring 18 having left and right-hand coils 19,20 with outer hook ends 21,22 and a connecting bar 23 therebetween. This form of spring (18) is specified for use as a front brake shoe return spring and, according to GMC specifications, has a free length of 8 11/16 inches and a stretch length of 9 13/32 inches with a 32-38 pounds-pull.

Figure 6:
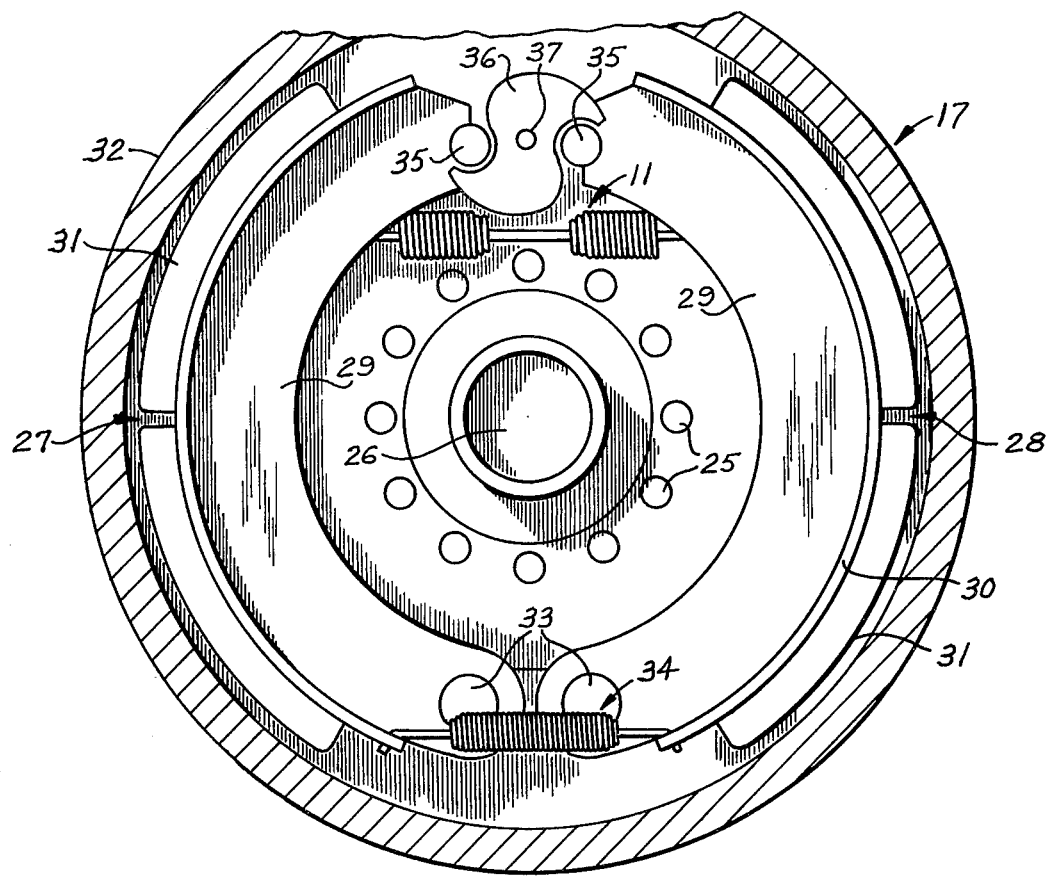
FIG. 6 is a diagrammatic cross-sectional view of a typical shoe brake illustrating the environmental use of a spring to be tested in the present apparatus.
Figure 7:
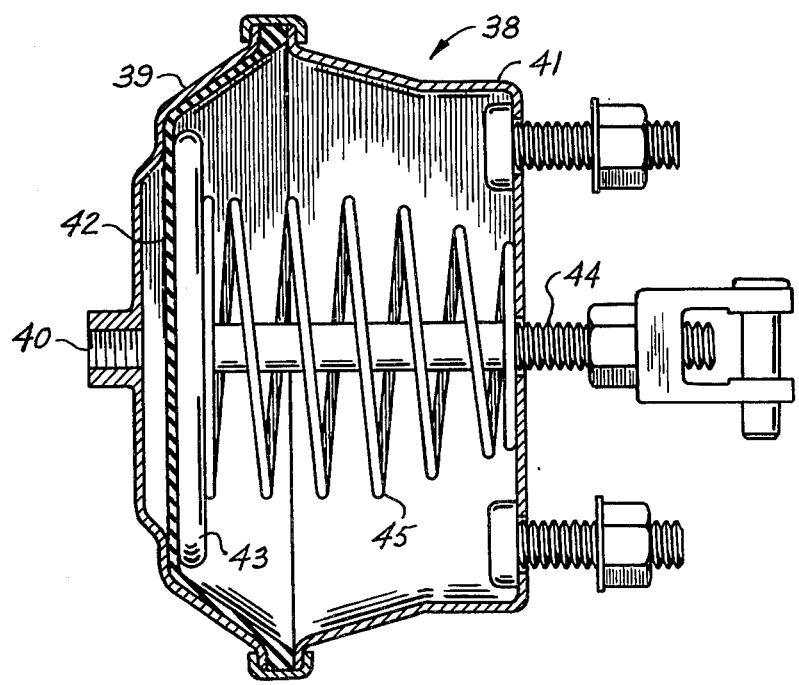
FIG. 7 is a diagrammatic cross-sectional view of a typical brake chamber illustrating still another environmental application of another spring to be tested by the present invention.

Referring to FIG. 6 illustrating the environmental usage of the rear return spring 11 (or front spring 18), a typical braking mechanism 17 includes a backing plate 24 bolted through apertures 25 to the vehicle axle 26. Interchangeable brake shoes 27,28 each have a web 29 and lining table 30 having friction lining 31 secured thereto for frictional engagement with a brake drum 32. The lower ends of the shoes 27,28 are articulated on hinge pins 33 and may have a balancing spring 34 extending therebetween. The upper actuation ends of the shoes 27,28 are provided with rollers 35 engaged against a cam 36 secured on a camshaft 37 adapted to be rotated through a typical slack adjuster (not shown) by a brake chamber actuator 38 (FIG. 7). The ends 14,15 of the rear brake shoe return spring 11 are hooked onto the webs 29 of the brake shoes 27,28 adjacent to the cam 36 and exert a retraction force maintaining the rollers 35 in engagement with the cam 36 before, during and after brake actuation. When the cam 36 is rotated to spread the upper shoe ends apart and outwardly to effect frictional engagement of the lining 31 with the drum 32, the spring 11 is stretched and also subjected to the heat generated within this confined area. As lining wear occurs, the spring 11 will be stretched even further unless the brakes are mechanically adjusted to re-position the shoe linings 31 relative to the drum 32, and even such adjustment may induce a stretched spring-set that can produce spring elongation. The importance of maintaining proper brake spring length and tension will be apparent, and it should also be understood that the return springs 11, 18 and 34 should have matched characteristics on each axle to obviate brake drag or uneven application and pulling.

Referring to FIG. 7 illustrating the brake chamber actuator 38 for rotating the camshaft 37 and cam 36 to drive the brake shoes 27,28 into braking engagement, the brake chamber 38 includes a housing having a pressure plate 39 with an air pressure inlet 40 and an upper housing (non-pressure) section 41 with a diaphragm 42 peripherally sealed therebetween. The diaphragm 42 is normally retracted against the pressure plate 39 by a diaphragm plate 43 connected to the push rod 44, which is coupled through the slack adjuster (not shown) to the camshaft 37 (FIG. 6). A compression spring 45 acts on the diaphragm plate 43 to effect such retraction of the diaphragm 42 for releasing the brakes. The GMC brake specifications for front retraction springs (45) require a retracted position compressive force of about 23-27 pounds and an increasing force of about 5½ to 7 pounds per inch of actuation stroke. Similarly, the rear retraction springs (45) have a zero stroke compressive force of 80-100 pounds with an increase of 20-24 pounds per inch of actuation stroke. It will thus be apparent that properly mated and tensioned brake chamber springs 45 are necessary to assure efficient brake operation.

Figure 1:
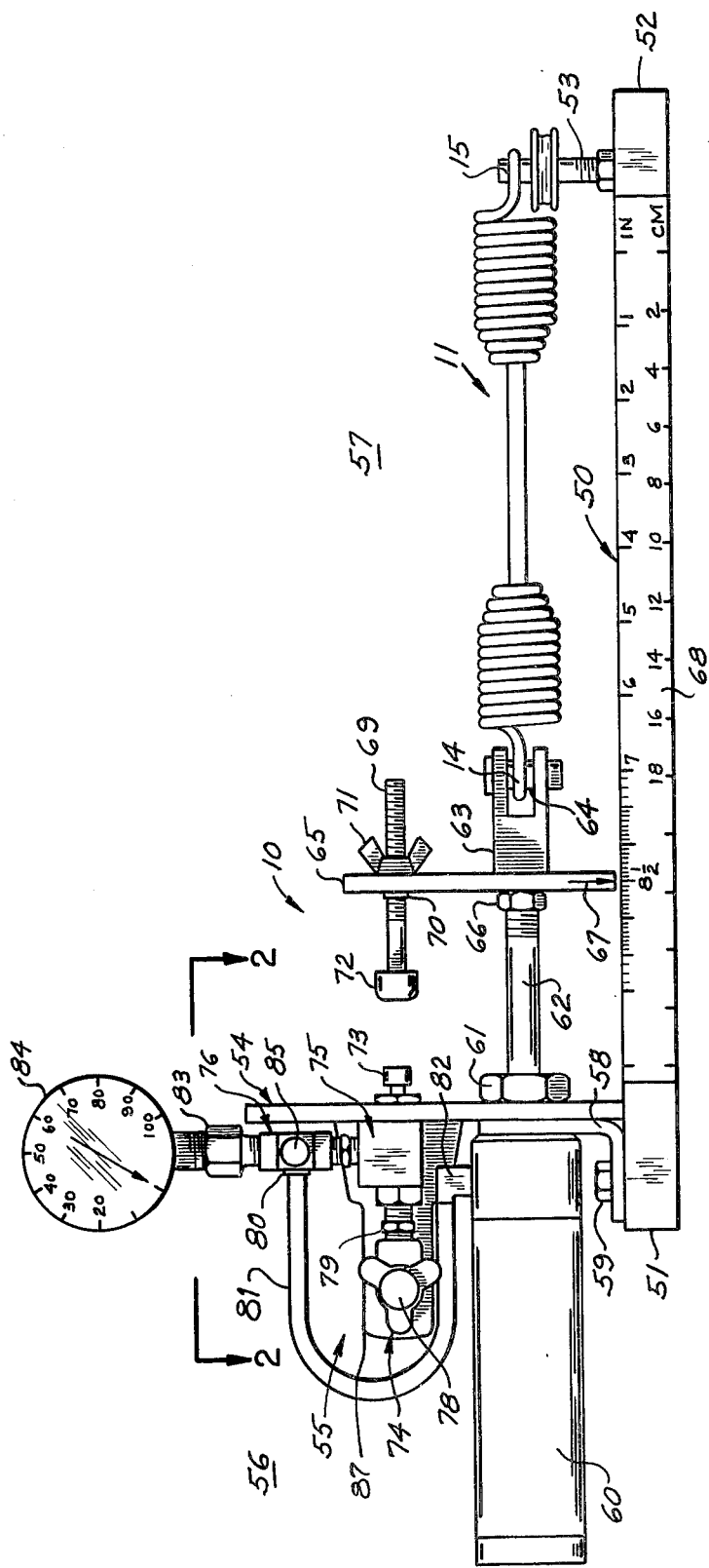
FIG. 1 is a side elevational view of a spring testing apparatus embodying the invention and showing a heavy duty, double coil spring positioned for testing.
Figure 2:
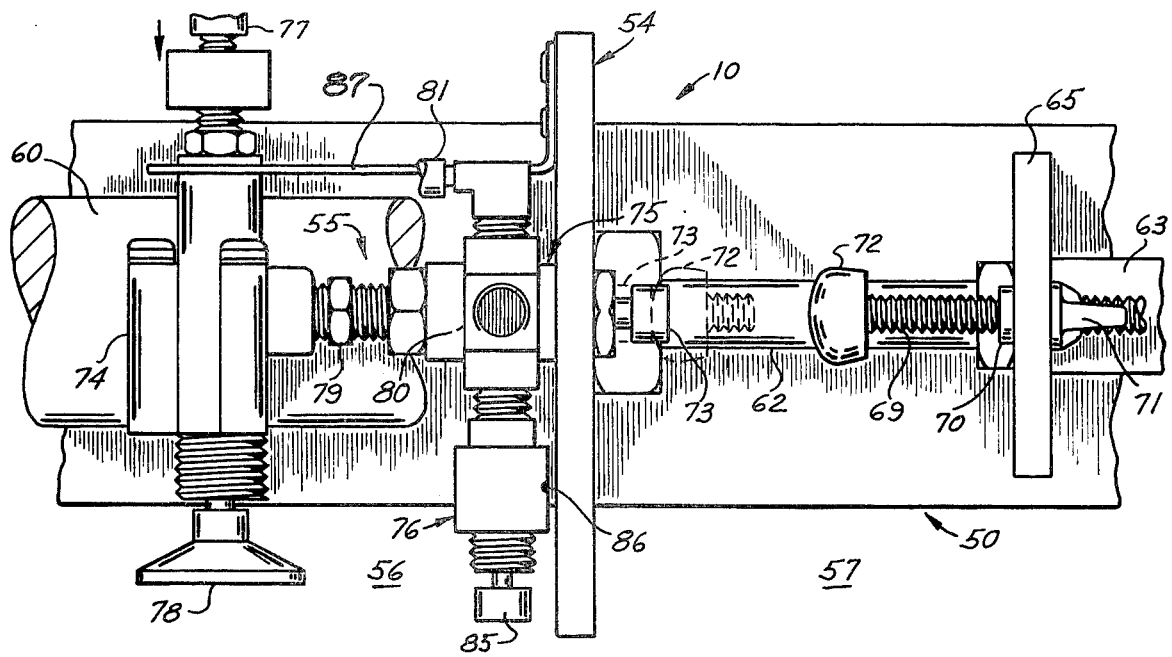
FIG. 2 is a fragmentary plan view of the spring testing apparatus as taken substantially along line 2—2 of FIG. 1 and showing an actuated position in phantom lines.

Referring now to FIGS. 1 and 2 of the drawings, for purposes of disclosure the heavy duty spring testing apparatus 10 embodying the invention is shown with a spring 11 assembled thereon for testing purposes. The apparatus 10 comprises an elongated, horizontal base frame member 50 having an actuation end 51 and an anchor end 52 with a fixed, upwardly projecting, anchor pin or stud 53 being secured adjacent to the anchor end and providing a fixed locus or reference point for orienting one end 15 of the spring 11, as will appear. The actuation end 51 of the base member 50 has a vertically extending panel member 54 mounted thereon to function as a primary support for a fluid pressure actuating system 55 and as a safety shield separating a manual valve control area 56 (to be described) from the spring testing area 57. A mounting bracket 58 is secured, as by bolts 59, to the base member 50 and receives one end of an actuation air cylinder 60 forming part of the actuation system 55. The panel member 54 abuts the opposite side of the bracket 58 and the air cylinder 60 and panel 54 are rigidly secured to the bracket 58 by a fastening nut 61. The piston rod 62 of the air cylinder 60 projects longitudinally of the base member 50 linearly toward the anchor pin 53, and a clevis 63 is carried on the end of the piston rod 62 with the clevis pin 64 forming a movable locus or reference point for orienting the other end 14 of the spring 11. A movable vertical panel 65 forming a secondary safety shield is secured in fixed relation to the piston rod 62 in abutment with the clevis 63, as by nut 66, and may be provided with an indicator 67 or other indicia associated with a ruler 68 on the base member 50 to directly read and establish the spring free-length measurement between the fixed and movable locus points 53 and 64 of the apparatus, as will be described more fully. The movable panel 65 also provides a mounting base for a longitudinally extending stroke adjustment member 69, which is threadedly secured to the panel 65 by a wing nut 71 or the like to position a free end abutment bumper or stop member 72 in preselected spaced relation with an air pressure shut-off or hold valve control button 73, also to be described more fully.

The actuation system 55 also comprises a series of valve members 74, 75 and 76 positioned in the valve control area 56 of the tester 10 and adapted to control fluid pressure communication between a compressed air or like fluid pressure source (not shown) and the air cylinder 60. The first valve 74 is a normally closed air switch having a quick connect inlet fitting 77 or the like (FIG. 2) for removable attachment to the compressed air source and having an internal valve element (not shown) manually controlled by a push button switch 78 for opening the valve to establish communication therethrough to an outlet coupling 79 connected to the inlet of the second valve 75. The second valve 75 has a normally open internal valve element (not shown) controlled by the hold button 73 during testing operations of the apparatus, and the outlet of the second valve is connected through a four-way connector 80 by air hose 81 to the inlet 82 of the air cylinder 60, by coupler 83 to an air pressure gauge 84 and also to the third valve member 76. The third valve member 76 has a normally closed internal valve element (not shown) normally preventing fluid communication therethrough, and is actuated by a manual pressure release button 85 to exhaust pressure fluid from the system 55 through an exhaust port 86 in an air system (or to return pressure fluid back to a fluid reservoir in a hydraulic system). As shown, the pressure fluid actuation system 55 including the valves 74, 75 and 76, the connector 80 and gauge 84 are supported on the primary panel 54 by the second valve 75 which has its valve element control button 73 positioned in the spring testing area 57 of the apparatus 10 in linear opposed relation with the stroke control member 69-72. The system 55 may also be laterally supported by a bracket 87 secured to the primary panel 54 and extending into the control valve area 56, but it will be understood that other positions and arrangements of actuation system valving and parts may be provided.

The apparatus 10 is quite light and portable to any convenient location where a regulated pressure source of about 105-110 PSI, such as an air compressor (not shown) is available. A charged compressed air tank (not shown) may be provided for limited testing purposes. The base member 50 may be removably secured in a bench mounted vise (not shown) or may be permanently bench mounted if desired.

The operation of the heavy duty spring testing apparatus 10 will now be described and the construction and testing methods will be fully understood therefrom. In the pre-operational condition of the apparatus 10, the apparatus base 50 is securely bench or vise mounted for stability, a regulated air supply is attached to the inlet quick connect fitting 77 or the like, the main air switch 74 is in the outer "off" position and the actuation system 55 is evacuated. The air cylinder piston rod 62 typically is pre-adjusted to position the clevis pin 64 in predetermined spaced relation with the anchor pin 53 such as $8\frac{1}{2}$ inches to accommodate and measure the free length of a typical rear brake shoe spring 11, and this pre-selected measurement is directly readable from the indicia 67 to ruler 68 position. In other words, the ruler 68 may be located on the side or top of the base frame 50 with the zero reading of the "inch" or "centimeter" scales being positioned from the fixed locus 53 the same distance as the indicia mark 67 is from the movable locus point 64 whereby the pre-adjusted position of the movable safety panel 65 will provide a direct reading of the free length spacing between the relatively movable spring reference points 53,64.

In testing one of the springs 11, one end 14 is hooked in the pull rod clevis 63 against pin 64 and the other end 15 is slipped or pushed down over the fixed anchor pin 53, which may have a notch or peripheral groove providing a vertical alignment position for the spring end 15. The distance between the stroke control stop member 72 and the shut-off valve control button 73 is pre-adjusted to limit actuation of the pull rod 62 and clevis pin 64 to the specified stretch length of the spring 11 so that the indicia marker 67 will be moved only to 9 13/32 inches, i.e. the distance between the stroke control abutment 72 and depressed control switch button 73 is approximately 15/16 of an inch.

To check the tension of the spring 11, the air switch 78 is depressed to open the application valve 74 and establish pressure fluid communication through the valve 75, connector 80 and air line 81 to energize the air cylinder 60 to move the pull rod 62 and movable locus point 64 linearly to stretch the spring 11 until the stroke control member 72 engages the control valve switch 73 to cut off the air supply and trap the established air pressure in the actuation system 55. The pressure gauge 84 is calibrated to directly indicate the pressure in pounds/square inch (PSI). This measurement is converted to "pounds pull" utilizing a conversion chart calculated for the tension readings at different stroke lengths. For the 15/16 inch stretch length of the return springs 11 and 18, the following conversion table is used:

| Air Press | — | Lbs Pull | Air Press | — | Lbs Pull |
|---|---|---|---|---|---|
| 30 | — | 29 lbs | 66 | — | 87.3 lbs |
| 32 | — | 32.3 | 68 | — | 90.5 |
| 34 | — | 35.5 | 70 | — | 93.7 |
| 36 | — | 38.8 | 72 | — | 97 |
| 38 | — | 42 | 74 | — | 100 |
| 40 | — | 45 | 76 | — | 103.5 |
| 42 | — | 48 | 78 | — | 106.7 |
| 44 | — | 51.7 | 80 | — | 110 |
| 46 | — | 55 | 82 | — | 113 |
| 48 | — | 58 | 84 | — | 116 |
| 50 | — | 61 | 86 | — | 119.6 |
| 52 | — | 64.6 | 88 | — | 122.8 |
| 54 | — | 68 | 90 | — | 126 |
| 56 | — | 71 | 92 | — | 129 |
| 58 | — | 74 | 94 | — | 132.6 |
| 60 | — | 77.6 | 96 | — | 135.8 |

-continued

| Air Press | — | Lbs Pull | Air Press | — | Lbs Pull |
|---|---|---|---|---|---|
| 62 | — | 80.8 | 98 | — | 139 |
| 64 | — | 84 | 100 | — | 142 |

After the gauge reading is noted, the actuation system 55 is evacuated by depressing the release button 85 to open the release valve 76 through the exhaust port 86.

The operator then tags the spring 11,18 with the "pounds pull" measurement so that substantially identical springs can be matched for subsequent use. If mismatched springs are found during the servicing of brakes, the weak or elongated spring should be replaced with a matching spring or the entire set replaced. Springs 11 having a specified free length of 8½ inches will fit loosely on the reference pins 53,64 if they are too long or stretched and will measure at a lower "pounds pull" at their stretched length. However, front return springs 18 have a longer free length (8 11/16 inches), but are tested to the same stretched length as springs 11 without re-adjustment of the position of the stroke control member 69–72.

Figure 3:
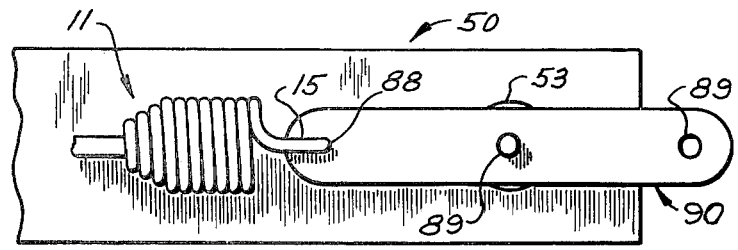
FIG. 3 is a fragmentary plan view illustrating an adapter for testing short springs.

Referring to FIG. 3, shorter brake springs of different lengths may be tested by using a simple adapter plate 90 provided with an opening 88 to receive the "fixed" spring end and having predeterminately spaced openings 89 to selectively be positioned on the fixed reference point 53 of the base member 50. The free length of the spring is thus accommodated between the relatively fixed and movable locus points for testing. However, specifications for shorter springs are not always available and a shorter stroke length of ½ inch has been found to be an acceptable test length for making comparative measurements and establishing an air pressure to "pounds pull" conversion table for purposes of mating such shorter springs.

Referring again to FIG. 7, brake chamber diaphragm springs 45 and similar compression springs are preferably tested in using the brake chamber assembly 38. For this purpose, a separate fixed anchor point is established by attaching the push rod 44 to the clevis 63 and securing the chamber housing 41 at a predetermined location relative to this movable locus point (a suitable bench mounted bracket may be provided for this purpose). A conversion chart based upon a 1 inch stroke will permit the checking of chamber springs 45 against the established specifications therefor.

The apparatus 10 is adaptable to the testing of other standard length springs by adjusting the free length relationship between the fixed and movable locus points 53,64. To this end, the nut 66 on the pull rod 62 is loosened and the clevis 63 is threadedly adjusted to move the indicia marker 67 on the safety panel 65 to the new measurement setting, and then re-securing the lock nut 66.

From the foregoing, it will be apparent that a simple, safe and accurate portable spring testing apparatus and its method of comparative spring testing has been provided to afford improved servicing and installation procedures for heavy duty brake springs and the like. It will be understood that disclosure of the preferred embodiment is given only by way of illustration and example, and the invention is only limited by the scope of the claims which follow.

What is claimed is:

1. A spring testing apparatus for the comparative testing of heavy duty brake springs and the like having prescribed specifications for the free and tension lengths between attachment hook ends thereof and for the tension force thereof at the tension length, a horizontal base member having an anchor end with fixed pin means adjacent thereto for orienting one attachment hook end of a spring to be tested and an actuation end with movable actuation pin means adjacent thereto for orienting the other attachment hook end of the spring, means for adjusting the distance between said fixed and movable pin means to accommodate the prescribed free length of the spring, and a pressure system including pressure exerting means adjacent to the base member actuation end for axially moving the actuation pin means in a linear horizontal direction relative to said anchor end pin means, first valve means for establishing substantially instantaneous fluid pressure communication between a pressure source greater than the tension force of the spring and said pressure exerting means, normally open second valve means between said first valve means and said pressure exerting means, a stroke control member longitudinally adjustable relative to said actuation pin means and being movable therewith for actuating said second valve means to trap pressure fluid in said pressure exerting means and for limiting linear movement of said actuation pin means relative to said anchor pin means, gauge means in fluid communication with said pressure exerting means and other means for releasing pressure in said pressure system, whereby brake springs of substantially equal tension force at the prescribed stretch length therefor can be determined for providing matched sets of such brake springs for same axle brake installation.

2. The spring testing apparatus according to claim 1, including a movable, non-rotatable safety panel member attached to said actuation pin means and said stroke control member being horizontally adjustably mounted on said movable safety panel and being maintained in alignment with said second valve means thereby.

3. The spring testing apparatus according to claim 1, including a primary safety panel secured to said base member, and said pressure system being substantially entirely positioned on the side of said primary safety panel remote from said fixed and movable spring orienting means.

4. The spring testing apparatus according to claim 1, in which said means for adjusting the distance between said fixed and movable pin means comprises adaptor means engagable with one of said fixed and movable pin means and having spring attachment hook end connecting means in predetermined spaced relation with the other of said fixed and movable pin means for accommodating another spring having a different prescribed free length.

5. A spring testing apparatus for testing heavy duty brake springs and the like, comprising an elongated horizontal base member having anchor and actuation ends; a vertical, primary support, safety panel secured to said base member and defining a spring testing area on the anchor side thereof and a control valve area on the actuation side thereof; an air pressure actuating system positioned in said control valve area including air motor means, first valve means for establishing air pressure communication between a compressed air source and said air motor means, and pressure gauge means for indicating the pressure applied in said air motor; spring orienting means positioned in said spring testing area including anchor means forming a fixed locus point for attaching one end of a spring to be tested, actuation means forming a movable locus point for attaching the other end of the spring, and coupling means extending between said actuation means and said air motor and being movable by the latter for effecting relative movement of said actuation means away from said anchor means; second valve means serially connected to said first valve means in the air pressure communication to said air motor, and adjustable means responsive to movement of said actuation means for operating said second valve means to interrupt said air pressure communication while maintaining the established air pressure acting on said air motor and gauge means; and third valve means connected on the downstream side of said second valve means and adapted to exhaust said air pressure system.

6. A method for the comparative testing and mating of springs to provide matched spring sets having substantially equal size, length and tension characteristics conforming to prescribed specifications therefor, comprising the steps of orienting opposite ends of a spring at relatively fixed and movable locus points corresponding to the prescribed free length specification of the spring, adjusting the movable distance of the movable locus point to correspond to the prescribed tension length specification of the spring, applying a pressure force from a pressure source substantially greater than the prescribed tension force of the spring to the movable locus point and substantially instantaneously moving such locus point the movable distance to tension the spring to its prescribed tension length, trapping the applied pressure force to hold the spring under tension and determining the tension force thereof, and releasing the applied pressure force.

* * * * *